United States Patent
Wolfert et al.

(10) Patent No.: US 6,821,396 B2
(45) Date of Patent: Nov. 23, 2004

(54) PROCESS FOR FRACTIONATING WATER-CONTAINING CRUDE AMINE MIXTURES FROM AMINE SYNTHESIS

(75) Inventors: Andreas Wolfert, Bad Rappenau (DE); Heinz Rütter, Hochdorf-Assenheim (DE); Stefan Rittinger, Pahang (MY); Mark Wehinger, Ludwigshafen (DE); Aurelie Alemany, Mannheim (DE); Willi Schmidt, Ludwigshafen (DE)

(73) Assignee: BASF Aktiengesellscahft, Ludwigshafen (DE)

( * ) Notice: Subject to any disclaimer, the term of this patent is extended or adjusted under 35 U.S.C. 154(b) by 0 days.

(21) Appl. No.: 10/272,012

(22) Filed: Oct. 17, 2002

(65) Prior Publication Data

US 2003/0089592 A1 May 15, 2003

(30) Foreign Application Priority Data

Oct. 30, 2001 (DE) .......................... 101 53 410

(51) Int. Cl.⁷ .......................... B01D 3/14; C07C 209/84
(52) U.S. Cl. .............................. 203/43; 203/14; 203/78; 203/80; 203/99; 203/DIG. 19; 564/497
(58) Field of Search .......................... 203/99, DIG. 19, 203/14, 43, 78, 80, 37; 564/497, 499

(56) References Cited

U.S. PATENT DOCUMENTS

| | | | |
|---|---|---|---|
| 2,690,378 A | * | 9/1954 | Penneman .................. 423/407 |
| 4,152,219 A | | 5/1979 | Newton et al. ................ 203/74 |
| 5,035,775 A | * | 7/1991 | Quackenbush et al. ........ 203/12 |
| 5,074,967 A | * | 12/1991 | Fowlkes ....................... 203/14 |
| 5,175,369 A | * | 12/1992 | Fowlkes ...................... 564/497 |
| 5,192,399 A | * | 3/1993 | Sieja ........................... 203/36 |
| 5,910,612 A | | 6/1999 | Simon et al. ............... 564/497 |

FOREIGN PATENT DOCUMENTS

| | | |
|---|---|---|
| DE | 27 23 474 | 12/1977 |
| DE | 29 02 302 | 7/1979 |
| EP | 0 881 211 | 12/1998 |
| GB | 1 102 370 | 2/1968 |
| GB | 2 012 757 | 8/1979 |

* cited by examiner

Primary Examiner—Virginia Manoharan
(74) Attorney, Agent, or Firm—Keil & Weinkauf

(57) ABSTRACT

A mixture containing mixture one or more amines, water, low-boilers and high-boilers, is fractioned in a process wherein
(i) low-boilers are separated from the mixture by distillation,
(ii) high-boilers are separated from the mixture by distillation,
(iii) the mixture is extracted with a sodium hydroxide solution to form an aqueous, sodium-hydroxide-containing first phase and an aqueous-organic, amine-containing second phase, and
(iv) the aqueous-organic second phase is distilled to form an amine/water azeotrope and an essentially anhydrous amine, and the amine/water azeotrope is recycled to the extraction step (iii).

7 Claims, 2 Drawing Sheets

PROCESS FOR FRACTIONATING WATER-CONTAINING CRUDE AMINE MIXTURES FROM AMINE SYNTHESIS

The invention relates to a process for fractionating a mixture which comprises one or more amines, water, low-boilers with or without high-boilers.

In the reaction of ammonia, primary or secondary amines with alcohols or with aldehydes in the presence of hydrogen, a reaction product produced, inter alia, is water, which frequently forms an azeotropic amine/water mixture with the product amine formed. In addition, the product mixture comprises low-boilers having a lower boiling point than that of the amine/water azeotrope, for example unreacted ammonia, or starting amine, and high-boilers having a higher boiling point than that of the product amine, for example higher-molecular-weight byproducts.

GB 1,102,370 describes a process for extractive distillation of an ethylenediamine/water mixture in which, in a first distillation column, the ethylene/water crude mixture is evaporated and the ascending vapor is brought into contact with aqueous sodium hydroxide solution flowing in countercurrent. At the top of the first column a low-water ethylenediamine/water mixture is obtained which has an amine concentration above the azeotropic point, which mixture is further distilled by simple rectification in a second column. At the top of the second column, pure ethylenediamine is obtained and at the bottom of the second column an ethylenediamine/water mixture is obtained which is combined with the crude mixture and recycled to the extractive distillation.

DE-A 29 02 302 describes a process for separating ethylarnine mixtures in which a diethylamine-, triethylamine-, ethanol-, water- and possibly monoethylamine-containing mixture is extracted with water and a water-immiscible solvent, an aqueous phase and a water-immiscible phase being obtained. The two phases are separated and further worked up by distillation. Water-immiscible solvents used are n-butane, n-hexane and cumene.

DE-A 27 23 474 describes a process for fractionating a water-, monoethylamine-, diethylamine- and triethylamine-containing mixture, in which an essentially anhydrous mixture of monoethylamine and diethylamine and triethylamine is separated off by distillation and, by distillation, monoethylamine is separated off from the anhydrous mixture of monoethylamine and diethylamine.

EP-A 0 881 211 describes a process for preparing anhydrous 2-amino-1-methoxypropane in which, in an extraction step, a 2-amino-1-methoxypropane-containing aqueous reaction mixture is admixed with sodium hydroxide solution, forming a sodium-hydroxide-containing aqueous phase and a 1-amino-1-methoxypropane-containing phase, the aqueous phase is separated off and, in a distillation step, the 2-amino-1-methoxypropane-containing phase is distilled, an azeotrope of water and 2-amino-1-methoxypropane first being produced, which is recycled to the extraction step, and then anhydrous 2-amino-1-methoxypropane then being produced.

It is an object of the present invention to provide an improved process for fractionating water-containing crude amine mixtures from amine synthesis, which process is suitable for a multiplicity of different crude amine mixtures.

We have found that this object is achieved by a process for fractionating an amine-containing mixture which comprises one or more amines, water, low-boilers and high-boilers, having the steps (i) to (iv):

(i) separating off by distillation low-boilers from the amine-containing mixture,
(ii) separating off by distillation high-boilers from the amine-containing mixture,
(iii) extracting the amine-containing mixture with sodium hydroxide solution, producing an aqueous, sodium-hydroxide-containing first phase and an aqueous-organic, amine-containing second phase,
(iv) distilling the aqueous-organic second phase, producing and an essentially anhydrous amine, an amine/water azeotrope and recycling the amine/water azeotrope to the extraction step (iii).

Surprisingly, separating off high-boilers before carrying out extraction step (iv) avoids the unwanted formation of solids in the extractor. The inventive process is preferably carried out continuously.

The inventive process can be carried out in such a manner that, in the distillation step (iv), the amine/water azeotrope is produced first and then the essentially anhydrous amine is produced. "Amine" is also taken to mean a mixture of a plurality of amines.

In a preferred embodiment, in distillation step (iv), the amine/water azeotrope is produced as sidestream takeoff in the enrichment part of the distillation column and recycled to the extraction step (iii), and the essentially anhydrous amine is produced as sidestream takeoff in the stripping part of the distillation column, further low-boilers are produced as overhead takeoff and further high-boiler-containing amine is produced as bottom-phase takeoff.

The further high-boiler-containing amine produced as bottom-phase takeoff is preferably recycled to step (ii).

In a subsequent distillation step (v) the essentially anhydrous amine produced in step (iv) can be further fractionated.

In a further preferred embodiment, in distillation step (iv), the amine/water azeotrope is produced as sidestream takeoff in the enrichment part of the column and recycled to the extraction step (iii), and further low-boilers are produced as overhead takeoff and the essentially anhydrous amine is produced as bottom-phase takeoff.

In a subsequent distillation step (v), the essentially anhydrous amine produced in step (iv) can be further fractionated.

Removing a low-boiler fraction as overhead takeoff from the distillation column in step (iv) avoids accumulation of low-boilers due to recycling amine/water azeotrope to extraction step (iii) in the continuous procedure.

A downstream distillation step (v) is required to produce the pure amines, if the starting mixture comprises two or more amines which, with water, form azeotropes having very similar boiling points. Examples of this are azeotropes having boiling points which differ by no more than 10° C.

BRIEF DESCRIPTION OF THE DRAWINGS

With reference to FIG. 1, the reaction output of amine preparation which is to be fractionated is fed as inflow stream 1 to a low-boiler removal column a. Low-boilers are, for example, unreacted starting material amine. The low-boiler removal column is generally operated at a pressure of from 1 to 40 bar absolute, preferably from 10 to 30 bar absolute, and at a temperature of generally from −20 to 300° C., preferably from 30 to 250° C. The number of theoretical plates is generally from 3 to 80, preferably from 10 to 30.

Figure 1:
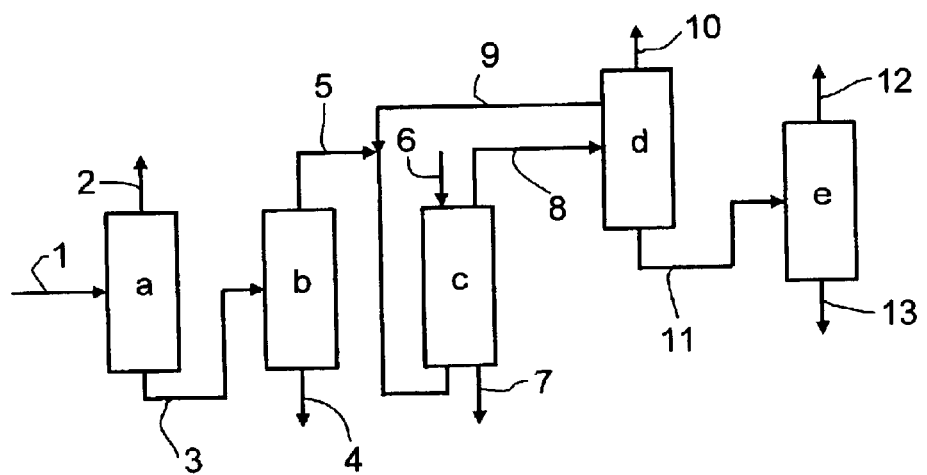
FIGS. 1 and 2 schematically illustrate two embodiments of the invention which are described in more detail below.

At the top of the low-boiler columna, a majority of the low-boilers are produced as overhead takeoff stream 2, which can be recycled to the amine synthesis. The bottom-phase takeoff stream 3 is fed to the high-boiler removal column b having generally from 3 to 80, preferably from 10 to 30, theoretical plates and distilled at a pressure of generally from 0.15 to 40 bar absolute, preferably from 1 to 5 bar absolute, and at a temperature of generally from −20 to 300° C., preferably from 30 to 250° C. As bottom-phase takeoff stream 4, high-boilers are produced which are discharged from the process. High-boilers are, for example, byproducts having a higher molecular weight than the desired product amines. As overhead takeoff stream 5 an amine/water azeotrope is produced which still comprises traces of low-boilers and high-boilers. As a result of the high-boiler removal, the solids formation does not occur in the downstream extractor c.

The overhead takeoff stream 5 is combined with the sidestream takeoff stream 9 of the azeotrope removal column d and fed to the extractor c. The extractor c can be of single or multistage design. A single-stage extractor c is, for example, a single mixer-settler extractor. Multistage extractors c are, for example, an extraction column or extractor cascade. Suitable extraction columns are, for example, packed columns, sieve-plate columns, cascade columns, pulsed columns, rotary columns and centrifugal columns. An extractor cascade is, for example, a plurality of series-connected mixer-settler extractors which can also be constructed in a space-saving manner as tower extractors or box extractors. Preferably, the extractor c is multistage, particularly preferably a countercurrent flow extraction column having generally from 1 to 25, preferably from 4 to 10, theoretical plates. These are generally operated at a pressure at which all components of the extraction mixture are above their boiling point. The temperature is selected in such a manner that none of the components of the extraction mixer is above its boiling point, and, in addition, a viscosity of both phases is established at which dispersion of the two phases is possible without problem. The temperature is generally from 5 to 200° C., preferably from 20 to 70° C., for example from 40 to 50° C. Sodium hydroxide solution is added as inflow stream 6. Generally, the concentration of the sodium hydroxide solution is from 1 to 75% by weight, preferably from 25 to 50% by weight. After phase separation the aqueous, sodium-hydroxide-containing phase is discharged from the process as effluent stream 7.

The aqueous-organic, amine-containing phase is fed as stream 8 to the azeotrope separation column d. The azeotrope separation column generally has from 3 to 80, preferably from 10 to 30, theoretical plates and is operated at a pressure of generally from 1 to 40 bar, preferably from 2 to 8 bar, and at a temperature of from −20 to 300° C., preferably from 50 to 120° C. In the enrichment part of this column an amine/water azeotrope is obtained as sidestream takeoff stream 9 and is combined with the overhead takeoff stream 5 of the high-boiler removal. Further low-boilers are obtained as overhead takeoff stream 10. As bottom-phase takeoff stream 11, anhydrous amine is obtained which can still comprise traces of high-boilers. The bottom-phase takeoff stream 11 can be further distilled in the distillation column e, with pure amine being obtained as overhead takeoff stream 12 and other high-boilers as bottom-phase takeoff stream 13.

Figure 2:
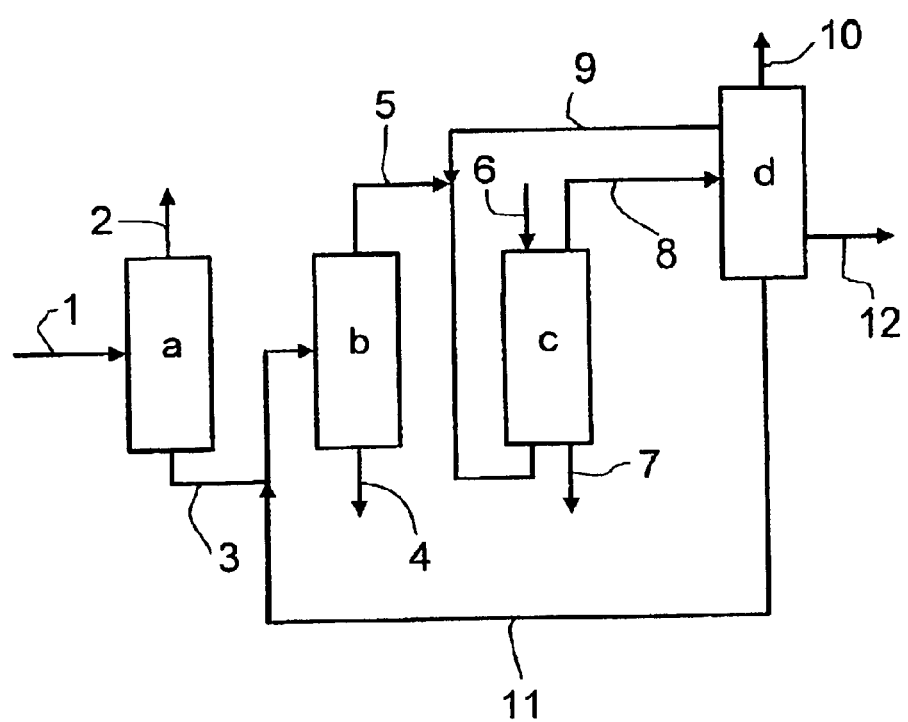

With reference to FIG. 2, a variant of the abovedescribed process is described. In this case, anhydrous amine is not taken off as bottom-phase takeoff stream from the azeotrope separation column, but as sidestream takeoff stream 12. As bottom-phase takeoff stream 11, an amine having an elevated content of high-boilers is taken off, combined with the bottom-phase takeoff stream 3 of the low-boiler removal and recycled to the high-boiler removal. Preferably, the bottom-phase takeoff stream 11 is from 0.1 to 20% by weight of the total of streams 11 and 12.

The sidestream takeoff stream 12 can be further fractionated in a downstream purifying distillation column. This is necessary to produce pure amines if two or more amines are present in the starting mixture, which form with water an azeotrope having very similar boiling points. Examples of such mixtures are N-methylmorpholine/N-ethylmorpholine/water, pyrrolidine/N-methylpyrrolidine/-water and piperidine/N-methylpiperidine/water.

The starting mixtures to be fractionated by the process according to the invention can vary greatly in their composition and generally comprise, per mol of product amine, from 0 to 9 mol, preferably from 0 to 3 mol, of low-boilers, from 1 to 10 mol, preferably from 1 to 4 mol, of water and, based on the total of all components of the starting mixture, from 2 to 20% by weight of high-boilers. Examples of starting mixtures to be fractionated by the process according to the invention are:

the product mixtures produced in the preparation of dimethylpropylamine from dimethylamine and propionaldehyde in the presence of hydrogen, or from dimethylamine and propanol. These can comprise, as low-boilers, unreacted dimethylamine and, formed from this by disproportionation, monomethylamine and trimethylamine. If the preparation starts from propionaldehyde, the starting mixture can comprise, as high-boilers, the compounds 2-methylpent-2-enaldehyde, 2-methylvaleraldehyde, dimethyl-(2-methylpent-2-enyl)amine and dimethyl(2-methylpentyl)amine which are formed by the reaction of two molecules of propionaldehyde and subsequent amination and/or hydrogenation.

the product mixture produced in the preparation of piperidine from 1,5-pentanediol and ammonia. This mixture can comprise unreacted ammonia as low-boiler. High-boilers which can be present are 2-methylpentanediol, dipiperidinylpentane and 2-methylpiperidine.

the product mixture produced in the preparation of N-methylpiperidine from 1,5-pentanediol and methylamine. As low-boilers, all of the abovementioned methylamines may be present. High-boilers are, for example, the reaction products of 1,5-pentanediol with one or two molecules of dimethylamine.

the product mixture obtained in the preparation of morpholine from diethylene glycol and ammonia. The low-boiler is ammonia, and the high-boiler is, for example, dimorpholino diglycol.

the product mixture obtained in the preparation of N-methylmorpholine from diethylene glycol and methylamine. Low-boilers which may be present are all of the abovementioned methylamines. High-boilers are, for example, the reaction products of diethylene glycol with one or two molecules of dimethylamine.

the product mixture produced in the preparation of pyrrolidine from 1,4-butanediol and ammonia. The low-boiler is ammonia, high-boilers are, for example, the products formed by further reaction of the resultant pyrrolidine with unreacted 1,4-butanediol.

the product mixture produced in the preparation of N-methylpyrrolidine from 1,4-butanediol and methylamine. Low-boilers which may be present are all of the abovementioned methylamines. High-boilers are, for example, the reaction products of 1,4-butanediol with one or two molecules of dimethylamine.

The invention is described in more detail by the example below.

EXAMPLE

The product mixture obtained in the synthesis of piperidine from ammonia and pentanediol is treated by the process according to FIG. 1. The mass flow rate and composition of the starting mixture (stream 1) and of the other streams occurring in the workup are reported in the table below. The mixture is distilled at 21 bar in a low-boiler removal column having 22 theoretical plates. At the top of the column ammonia is taken off (stream 2). The bottom temperature is 204° C. The top temperature is 46° C. The bottom-phase discharge of the low-boiler column (stream 3) is then distilled at 1 bar in a high-boiler removal column having 25 theoretical plates. At the bottom a stream is taken off (stream 4) which principally comprises dipiperidinylpentane, 2-methylpiperidine and 2-methylpentanediol. The overhead takeoff (stream 5) comprises water, piperidine and 2-methylpiperidine. The bottom temperature is 176° C. The top temperature is 95° C. The overhead takeoff stream of the high-boiler removal column is combined with the sidestream takeoff stream (stream 9) of the azeotrope distillation column and fed to the extraction column operating at atmospheric pressure and having 10 theoretical plates. The extraction is carried out at atmospheric pressure with 50% strength by weight sodium hydroxide solution which is added at the top of the extraction column. The bottom temperature is 55° C. The top temperature is 39° C. As organic phase, a low-water mixture of piperidine and 2-methylpiperidine, which has a residual water content of 2% by mass, is taken off at the top of the extraction column (stream 8), which is fed to the azeotrope distillation column having 18 theoretical plates. This operates at atmospheric pressure. The bottom temperature is 113° C. The top temperature is 95° C. At the third plate from the top, the azeotrope water/piperidine or water/2-methylpiperidine (stream 9) is taken off in the sidestream takeoff and combined with the overhead takeoff stream of the high-boiler removal. The bottom-phase takeoff stream (stream 11) of the azeotrope distillation column is fed to the purifying distillation column operating at atmospheric pressure. At the top of the purifying distillation column there is produced the product stream whose main component is piperidine (stream 12). At the bottom a stream (stream 13) is separated off which principally comprises 2-methylpiperidine. The bottom temperature is 123° C. The top temperature is 109° C. The process was run over a period of 40 days without solids formation in the extraction column and without accumulation of low-boilers.

TABLE

| Stream* | 1 | 2 | 3 | 4 | 5 | 8 | 9 | 10 | 11 | 12 | 13 |
|---|---|---|---|---|---|---|---|---|---|---|---|
| Water | 1.136 | 0.000 | 1.136 | 0.000 | 1.136 | 0.054 | 0.050 | 0.004 | 0.001 | 0.001 | 0.000 |
| NH$_3$ | 2.755 | 2.755 | 0.000 | 0.000 | 0.000 | 0.000 | 0.000 | 0.000 | 0.000 | 0.000 | 0.000 |
| Piperidine | 2.507 | 0.000 | 2.507 | 0.003 | 2.505 | 2.606 | 0.105 | 0.009 | 2.492 | 2.480 | 0.012 |
| 2-methyl-pentanediol | 0.104 | 0.000 | 0.104 | 0.104 | 0.000 | 0.000 | 0.000 | 0.000 | 0.000 | 0.000 | 0.000 |
| 2-methyl-piperidine | 0.084 | 0.000 | 0.084 | 0.044 | 0.040 | 0.040 | 0.000 | 0.000 | 0.040 | 0.003 | 0.037 |
| Dipiperidinyl-pentane | 0.098 | 0.000 | 0.098 | 0.098 | 0.000 | 0.000 | 0.000 | 0.000 | 0.000 | 0.000 | 0.000 |
| Total | 6.683 | 2.755 | 3.028 | 0.248 | 3.680 | 2.700 | 0.155 | 0.013 | 2.532 | 2.483 | 0.049 |

*Figures in kg/h

What is claimed is:

1. A process for fractionating an amine-containing mixture comprising at least one amine, water, low-boilers and high-boilers, wherein said process comprises
   (i) separating off by distillation low-boilers from the amine-containing mixture, and
   (ii) separating of f by distillation high-boilers from the amine-containing mixture, to produce a pretreated amine-containing mixture, and
   (iii) extracting the pretreated amine-containing mixture with sodium hydroxide solution to form an aqueous, sodium-hydroxide-containing first phase and an aqueous-organic, amine-containing second phase,
   (iv) distilling the aqueous-organic second phase in a distillation column having an enrichment part and a stripping part to form an amine-water azeotrop and an essentially anhydrous amine, and recycling the amine-water azeotrop to the extraction step (iii), and wherein, in step (iv), the amine-water azeotrop is obtained as a sidestream takeoff in the enrichment part of the distillation column and is recycled to the extraction step (iii), and the essentially anhydrous amine is obtained as a sidestream takeoff in the stripping part of the distillation column, further low-boilers are obtained as an overhead takeoff and further high-boiler-containing amine is obtained as a bottom phase takeoff.

2. A process as claimed in claim 1, wherein the further high-boiler-containing amine produced in step (iv) is recycled to step (ii).

3. A process as claimed in claim 1, wherein the essentially anhydrous amine produced in step (iv) is further fractionated by distillation in a subsequent step (v).

4. A process as claimed in claim 1, wherein the extraction step (iii) is carried out in multiple stages.

5. A process as claimed in claim 1, wherein the distillation column employed in step (iv) has from 3 to 80 plates and the distillation is conducted at a pressure of from 1 to 40 bar and at a temperature of from −20 to 300° C.

6. A process as claimed in claim 1, wherein the mixture to be fractionated is selected from the group consisting of product mixtures obtained in the manufacture of dimethylpropylamine from dimethylamine and propionaldehyde and hydrogen, of dimethylpropylamine from dimethylamine and propanol, of piperidine from 1,5-pentanediol and ammonia, of N-methylpiperidine from 1,5-pentanediol and methylamine, of morpholine from diethylene glycol and ammonia, of N-methylmorpholine from diethylene glycol and methylamine, of pyrrolidine from 1,4-butanediol and ammonia, and of N-methylpyrrolidine from 1,4-butanediol and methylamine.

7. A process as claimed in claim 1, which is carried out continuously.

* * * * *

UNITED STATES PATENT AND TRADEMARK OFFICE
CERTIFICATE OF CORRECTION

PATENT NO. : 6,821,396 B2
DATED : November 23, 2004
INVENTOR(S) : Woelfert et al.

It is certified that error appears in the above-identified patent and that said Letters Patent is hereby corrected as shown below:

Title page,
Item [75], Inventor, "Wolfert" should read -- Woelfert --.

Column 6,
Line 30, "separating of f by" should read -- separating off by --.

Signed and Sealed this

Twenty-ninth Day of March, 2005

JON W. DUDAS
*Director of the United States Patent and Trademark Office*